United States Patent
Smith et al.

(10) Patent No.: US 12,087,399 B2
(45) Date of Patent: Sep. 10, 2024

(54) SYSTEMS AND METHODS FOR CUSTOMIZING CELL CULTURE MEDIA FOR OPTIMIZED CELL PROLIFERATION BASED ON GENETIC TRAITS OF CELLS

(71) Applicant: Sapphiros AI Bio LLC, Boston, MA (US)

(72) Inventors: Robin Y. Smith, Boston, MA (US); Marcie A. Glicksman, Boston, MA (US)

(73) Assignee: Sapphiros AI Bio LLC, Boston, MA (US)

( * ) Notice: Subject to any disclaimer, the term of this patent is extended or adjusted under 35 U.S.C. 154(b) by 862 days.

(21) Appl. No.: 16/482,946

(22) PCT Filed: Feb. 1, 2018

(86) PCT No.: PCT/US2018/016382
§ 371 (c)(1),
(2) Date: Aug. 1, 2019

(87) PCT Pub. No.: WO2018/144693
PCT Pub. Date: Aug. 9, 2018

(65) Prior Publication Data
US 2020/0013481 A1    Jan. 9, 2020

Related U.S. Application Data

(60) Provisional application No. 62/453,274, filed on Feb. 1, 2017.

(51) Int. Cl.
  *G16B 20/20*   (2019.01)
  *C12N 5/00*    (2006.01)
  *C12Q 1/6881*  (2018.01)

(52) U.S. Cl.
  CPC ........... *G16B 20/20* (2019.02); *C12N 5/0018* (2013.01); *C12Q 1/6881* (2013.01); *C12N 2500/30* (2013.01); *C12N 2500/32* (2013.01); *C12N 2500/36* (2013.01); *C12N 2500/38* (2013.01); *C12Q 2600/156* (2013.01); *Y10S 423/05* (2013.01)

(58) Field of Classification Search
None
See application file for complete search history.

(56) References Cited

U.S. PATENT DOCUMENTS

| | | | |
|---|---|---|---|
| 7,920,994 B2 | 4/2011 | Palsson et al. | |
| 8,311,790 B2 | 11/2012 | Senger et al. | |
| 9,454,640 B2 | 9/2016 | Famili et al. | |
| 2006/0286668 A1* | 12/2006 | Price | C12N 5/06 435/325 |
| 2007/0254306 A1* | 11/2007 | Giampapa | C12Q 1/6883 702/20 |
| 2012/0191434 A1* | 7/2012 | Famili | G16B 5/00 703/11 |
| 2015/0175956 A1* | 6/2015 | Elhofy | A01N 1/0226 435/404 |
| 2016/0160270 A1* | 6/2016 | Herrgard | G16B 30/00 506/8 |
| 2016/0171159 A1 | 6/2016 | Smith | |
| 2020/0013481 A1 | 1/2020 | Smith et al. | |

OTHER PUBLICATIONS

MTHFR. NIH: National Library of Medicine. https://www.ncbi.nlm.nih.gov/gene/122899460 (accessed Jul. 2022). pp. 1-4. (Year: 2021).*
Zinck, John et al., "Approached for the identification of genetic modifiers of nutrient dependent phenotypes: examples from folate", Frontiers in Nutrition, vol. 1, Article 8, pp. 1-10. (Year: 2014).*
ThermoFisher Scientific, "21875-RPMI 1640 Media Formulation", Webpage. https://www.thermofisher.com/us/en/home/technical-resources/media-formulation.187.html. Accessed: Feb. 2, 2023. (Year: 2023).*
International Preliminary Report on Patentability for International Application No. PCT/US2018/016382 dated Aug. 6, 2019, pp. 1-6.
International Search Report and Written Opinion for International Application No. PCT/US2018/016382 dated May 15, 2018, pp. 1-8.
Lewis et al., "Genomic landscapes of Chinese hamster ovary cell lines as revealed by the Cricetulus griseus draft genome," Nat Biotech 31(8):759-765 (2013).

* cited by examiner

*Primary Examiner* — Michelle F. Paguio Frising
*Assistant Examiner* — Grant C Currens
(74) *Attorney, Agent, or Firm* — Foley Hoag LLP; Erik A. Huestis; Sameer K. Pai

(57) ABSTRACT

Described herein are various systems and methods for customizing cell culture media for optimized cell proliferation based on genetic traits of the cells. Factors of the cells, such as genetics, can determine the optimum cell culture conditions for growth and use of individual cells in vitro. In certain embodiments, genetics can determine sensitivity from a toxic perspective. In certain embodiments, genetics can determine what concentration(s) of growth factor(s) and nutrient(s) are required for optimum growth.

18 Claims, 4 Drawing Sheets

ACCESSING, BY A PROCESSOR OF A COMPUTING DEVICE, GENOTYPING DATA CORRESPONDING TO A POPULATION OF CELLS, SAID GENOTYPING DATA INFORMATIVE OF ONE OR MORE GENETIC TRAITS OF THE POPULATION OF CELLS, WHEREIN THE ONE OR MORE GENETIC TRAITS COMPRISES AT LEAST ONE MEMBER SELECTED FROM THE GROUP CONSISTING OF APOPTOSIS, PROLIFERATION, GENOME INSTABILITY, AND ACIDOSIS

AUTOMATICALLY IDENTIFYING, BY THE PROCESSOR, A COMPOSITION FOR A CELL CULTURE MEDIA BASED AT LEAST IN PART ON THE GENOTYPING DATA, SAID COMPOSITION SELECTED FOR ADVANTAGEOUS GROWTH OF THE POPULATION OF CELLS

CONTACTING THE POPULATION OF CELLS WITH THE CELL CULTURE MEDIA TO GROW THE POPULATION OF CELLS

FIG. 4

SYSTEMS AND METHODS FOR CUSTOMIZING CELL CULTURE MEDIA FOR OPTIMIZED CELL PROLIFERATION BASED ON GENETIC TRAITS OF CELLS

CROSS REFERENCE TO RELATED APPLICATIONS

This application claims the benefit of U.S. Provisional Application No. 62/453,274 filed Feb. 1, 2017, the contents of which are hereby incorporated by reference herein in their entirety.

TECHNICAL FIELD

The invention relates generally to systems and methods of customizing cell culture media. More particularly, in certain embodiments, the invention relates to systems and methods for customizing cell culture media for optimized cell proliferation based on genetic traits of cells.

BACKGROUND

Cell culture media comprises many different components and is specialized for the cell type based on requirements needed to optimize cell growth. For example, basal media, which is often used for standard cell lines that do not have many requirements, has a long storage life and no growth components added. Basal media contains, for example, glucose, pyruvate, and amino acids. Additives to cell culture media can include conditioned media, which contains factors that are secreted by cells such as bio-active growth factors, proteins, and cytokines.

Conditioned media may not be rigidly defined as it is taken from the supernatant from cells that are growing. Some media requires serum and is less defined; other media is defined and does not include serum but has defined concentrations of nutrients, growth factors, and cytokines. As a result, cell culture practices often involve custom media for specific cell lines or experimental protocols.

Custom media are utilized for a variety of reasons. For example, in some cases, standard catalog media products do not generate adequate results for a particular cell line or application of that cell line. In other cases, custom media are required for assays, which are compromised by specific components of standard media that will interfere with the media components. Customized media can be prepared with these components omitted.

The selection of cell culture media is largely determined by trial-by-error to see what culture media appears to keep cells alive and growing. Unfortunately, each cell line may respond differently to different cell culture media, thereby generating variation in experiments, or increasing time and costs that are incurred by the trial-by-error method.

Thus, systems and methods are needed to facilitate selection of customized cell culture media for individual cell lines.

SUMMARY

Presented herein are systems and methods for customizing cell culture media for optimized cell proliferation based on genetic traits of the cells. In certain embodiments, the systems and methods described herein provide relationships that correspond particular variations that may occur in a population of cell's DNA (e.g., variants of different specific SNPs, or other genotyping data) to related genetic traits and/or phenotypes that they influence (e.g., cell proliferation, e.g., toxicity, e.g., apoptosis).

In certain embodiments, genotyping data determined from a biological sample provided by a population of cells is used as a basis for identification of cell culture media supplements (e.g., albumins and transport proteins, e.g., antibiotics, e.g., cytokines and growth factors, e.g., hormones, e.g., amino acids, e.g., vitamins) that are relevant for a given population of cells due to their particular genetic makeup. For example, different cell lines comprising a population of cells have different variants of particular SNPs, each SNP associated with one or more particular genes. For a given SNP corresponding to a given gene, the particular variant that a population of cells has influences a specific genetic trait and/or phenotype. These phenotypes may be related to a population of cell's propensity to proliferate, their ability to process certain vitamins, their ability to produce proteins for cellular functions and maintenance (e.g., related to genome stability), and their sensitivity towards toxic substances (e.g., bacterial or viral contaminations).

Accordingly, based on the various different SNP variants a population of cells has (and/or based on other genotyping data corresponding to the population of cells), certain cell culture media supplements or combinations thereof may be useful for that population of cells. For example, if a population of cells has a particular variant of a SNP that causes the cell line to require a higher or lower level of Vitamin B12 (e.g., a SNP associated with the FUT2 gene), then it would be valuable for the population of cells to be cultured in media that has a higher or lower level of Vitamin B12 (based on the particular FUT2 SNP) that helps to optimize the proliferation of the cells. For example, if a cell population has a particular variant of a SNP that causes the population of cells to have a reduced ability to convert beta carotene to retinol, the population of cells may benefit from being cultured in a cell culture media with increased Vitamin A concentration. Similarly, depending on whether a population of cells has particular SNP variants that influence genomic repair, proliferation, or apoptosis, different cell culture media supplements may be identified that would benefit the population of cells.

Based on genotyping data, various relevant cell culture media supplements that are of particular benefit to the population of cells can be identified. In certain embodiments, the identified cell culture media supplements can be provided (e.g., displayed, e.g., displayed via a graphic user interface) to a user who is culturing the population of cells.

In certain embodiments, where the genotyping data is based on SNP variants associated with identified traits, one or a combination of cell culture media products may be automatically recommended according to one or more identified traits (e.g., via reference to a look-up table or other mapping). In certain embodiments, the recommended cell culture media products are provided (e.g., displayed, e.g., displayed via a graphic user interface) to the user who is culturing the population of cells.

In one aspect, the invention is directed to a method comprising: obtaining genotyping data corresponding to a population of cells, said genotyping data informative of one or more genetic traits of the population of cells, wherein the one or more genetic traits comprises at least one member selected from the group consisting of apoptosis, proliferation, genome instability, and acidosis; identifying a composition for a cell culture media based at least in part on the genotyping data, said composition selected for advantageous growth of the population of cells; and contacting the population of cells with the cell culture media to grow the population of cells.

In another aspect, the invention is directed to a method comprising: accessing, by a processor of a computing device, genotyping data corresponding to a population of cells, said genotyping data informative of one or more genetic traits of the population of cells, wherein the one or more genetic traits comprises at least one member selected from the group consisting of apoptosis, proliferation, genome instability, and acidosis; automatically identifying, by the processor, a composition for a cell culture media based at least in part on the genotyping data, said composition selected for advantageous growth of the population of cells; and contacting the population of cells with the cell culture media to grow the population of cells.

In certain embodiments, the method is an in vitro method.

In certain embodiments, identifying a composition comprises: adjusting a level of one or more albumin and/or transport proteins in the cell culture media based on the genotyping data of the population of cells.

In certain embodiments, one or more albumin and/or transport proteins comprise a member selected from the group consisting of albumin human recombinant, bovine serum albumin (BSA), fetal bovine serum (FBS), conalbumin, fetuin from FBS, bovine transferrin, transferrin from human serum, apo-transferrin bovine, holo-transferrin bovine, and holo-transferrin human.

In certain embodiments, identifying a composition comprises: adjusting a level of one or more antibiotics in the cell culture media based on the genotyping data of the population of cells.

In certain embodiments, the one or more antibiotics comprise a member selected from the group consisting of Actinomycin D, Amphotericin B, Ampicillin, Carbenicillin, Chloramphenicol, Erythromycin, G 418, Gentamicin, Guanidine, Hygromycin B, Kanamycin, Mitomycin C, Mycophenolic acid, Neomycin, Nystatin, Penicillin G, Penicillin G, Polymyxin B, Puromycin, Spectinomycin, Streptomycin, and Streptomycin.

In certain embodiments, identifying a composition comprises: adjusting a level of one or more cytokines and/or growth factors in the cell culture media based on the genotyping data of the population of cells.

In certain embodiments, the one or more cytokines and/or growth factors comprise a member selected from the group consisting of epidermal growth factors and Neuregulin (NRG) family members, fibroblast growth factors, growth factor analogs, hematopoietic cytokines, hepatocyte growth factor/scatter factors, humankine growth factors and cytokines, insulin-like growth factors, interleukins, macrophage inflammatory proteins, neurotrophic factors, platelet derived growth factors and hormones, transforming growth factors, tumor necrosis factor and family members, and vascular endothelial growth factor.

In certain embodiments, identifying a composition comprises: adjusting a level of one or more hormones in the cell culture media based on the genotyping data of the population of cells.

In certain embodiments, the one or more hormones comprise a member selected from the group consisting of Dexamethasone, Erythropoietin, β-Estradiol, Hydrocortisone, Insulin, Progesterone, Prolactin (human), Somatostatin, L-Thyroxine, and 3,3',5-Triiodo-L-thyronine.

In certain embodiments, identifying a composition comprises: adjusting a level of one or more lipids and/or lipid carriers in the cell culture media based on the genotyping data of the population of cells.

In certain embodiments, the one or more lipids and/or lipid carriers comprise a member selected from the group consisting of cyclodextrins, Arachidonic acid, Cholesterol, Cod liver oil fatty acid methyl esters, Fatty Acid Supplements, Linoleic acid, Linoleic Acid-Oleic Acid-Albumin, and Oleic Acid.

In certain embodiments, identifying a composition comprises: adjusting a level of one or more amino acids in the cell culture media based on the genotyping data of the population of cells.

In certain embodiments, the one or more amino acids comprise a member selected from the group consisting of N-Acetyl-L-cysteine, Ala-Gln, L-Alanine, L-Arginine, L-Asparagine, L-Cysteine, L-Glutamic acid, DL-Glutamic acid, L-Glutamine, L-Glutathione, Glycine, L-Histidine, trans-4-Hydroxy-L-proline, L-Isoleucine, L-Leucine, L-Lysine, L-Methionine, DL-Methionine, L-Phenylalanine, L-Proline, L-Serine, DL-Serine, L-Threonine, DL-Threonine, L-Tryptophan, L-Tyrosine, L-Valine.

In certain embodiments, identifying a composition comprises: adjusting a level of one or more vitamins in the cell culture media based on the genotyping data of the population of cells.

In certain embodiments, the one or more vitamins comprise a member selected from the group consisting of L-ascorbic acid, biotin powder, Menadione sodium bisulfate, pyridoxamine dihydrochloride, retinyl acetate, RPMI 1640 Vitamins, (+)-Sodium L-ascorbate, and Beta Carotene, Vitamin A, Vitamin B12, Vitamin D, Folate levels, Vitamin B6, Vitamin E, and Vitamin C.

In certain embodiments, the method comprises determining sensitivity of the population of cells to any of the following: transport proteins, antibiotics, growth factors, hormones, amino acids, and/or vitamins.

In certain embodiments, the genotyping data comprises measurements of one or more SNPs (e.g., wherein the one or more SNPs comprise(s), for each SNP, a first measurement that identifies a first nucleotide of a first copy (e.g., from a first of two sets of chromosomes) of the population of cell's genetic material, and a second measurement that identifies a second nucleotide of a second copy (e.g., from a second of two sets of chromosomes) of the population of cell's genetic material).

In certain embodiments, the one or more SNPs comprise a member selected from the group consisting of FADS1, KCTDIO, PPARg, BCM01, FUT2, GC, MTHR, NBF2, RSU1, and SLC23A1. In certain embodiments, the one or more SNPs affects a cellular function encoded by a DNA repair gene, a cellular maintenance gene, a cell growth gene, or a cell cycle gene.

In certain embodiments, the genotyping data comprises data collected from a PCR-based SNP genotyping assay.

Elements of embodiments involving one aspect of the invention (e.g., methods) can be applied in embodiments involving other aspects of the invention, and vice versa.

Definitions

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising"

and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art.

"Gene": A "gene," as used herein, refers to a DNA region (e.g., including exons and introns) encoding a gene product, in addition to all DNA regions that regulate the production of the gene product (regardless of whether such regulatory sequences are adjacent to coding and/or transcribed sequences). Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites, and locus control regions.

"Nucleic acid" and "Polynucleotide": The terms "nucleic acid" and "polynucleotide" refer to a deoxyribonucleotide or ribonucleotide polymer, in linear or circular conformation. Without wishing to be bound to any theory, these terms are not to be construed as limiting with respect to the length of a polymer. The terms can encompass known analogs of natural nucleotides, as well as nucleotides that are adjusted in the base, sugar and/or phosphate moieties. In general, an analog of a particular nucleotide has the same base-pairing specificity (i.e., an analog of A will base-pair with T, i.e., an analog of G will base-pair with C). The nucleotides of a nucleic acid or polynucleotide can be linked by phosphodiester, phosphothioate, phosphoramidite, phosphorodiamidate bonds, or combinations thereof.

"Nucleotide": The term "nucleotide" refers to deoxyribonucleotides or ribonucleotides. The nucleotides can be standard nucleotides (i.e., adenosine, guanosine, cytidine, thymidine, and uridine) or nucleotide analogs. A nucleotide analog refers to a nucleotide having an adjusted purine or pyrimidine base or an adjusted ribose moiety. A nucleotide analog may be a naturally occurring nucleotide (e.g., inosine) or a non-naturally occurring nucleotide. Non-limiting examples of modifications on the sugar or base moieties of a nucleotide include the addition (or removal) of acetyl groups, amino groups, carboxyl groups, carboxymethyl groups, hydroxyl groups, methyl groups, phosphoryl groups, and thiol groups, as well as the substitution of the carbon and nitrogen atoms of the bases with other atoms (e.g., 7-deaza purines). Nucleotide analogs also include dideoxy nucleotides, 2'-O-methyl nucleotides, locked nucleic acids (LNA), peptide nucleic acids (PNA), and morpholinos.

"Sample": The term "sample", as used herein, refers to a biological sample obtained or derived from a source of interest, as described herein. In certain embodiments, a source of interest comprises an organism, such as a microbe, a plant, an animal or a human. In certain embodiments, a biological sample is or comprises biological tissue or fluid. In certain embodiments, a biological sample may be or comprise bone marrow; blood; blood cells; ascites; tissue or fine needle biopsy samples; cell-containing body fluids; free floating nucleic acids (e.g., cell free DNA); sputum; saliva; urine; cerebrospinal fluid, peritoneal fluid; pleural fluid; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In certain embodiments, a biological sample is or comprises cells obtained from an individual. In certain embodiments, obtained cells are or include cells from an individual from whom the sample is obtained. In certain embodiments, a sample is a "primary sample" obtained directly from a source of interest by any appropriate means. For example, in certain embodiments, a primary biological sample is obtained by methods selected from the group consisting of a swab, biopsy (e.g., fine needle aspiration or tissue biopsy), surgery, collection of body fluid (e.g., blood, lymph, feces etc.), etc. In certain embodiments, as will be clear from context, the term "sample" refers to a preparation that is obtained by processing (e.g., by removing one or more components of and/or by adding one or more agents to) a primary sample. For example, filtering using a semi-permeable membrane. Such a processed "sample" may comprise, for example nucleic acids or proteins extracted from a sample or obtained by subjecting a primary sample to techniques such as amplification or reverse transcription of mRNA, isolation and/or purification of certain components, etc.

Drawings are presented herein for illustration purposes, not for limitation.

BRIEF DESCRIPTION OF DRAWINGS

The foregoing and other objects, aspects, features, and advantages of the present disclosure will become more apparent and better understood by referring to the following description taken in conduction with the accompanying drawings, in which:

FIG. 4 shows a method for customizing cell culture media for optimized cell proliferation based on genetic traits of the cells, according to an illustrative embodiment of the invention.

DETAILED DESCRIPTION

Figure 1:
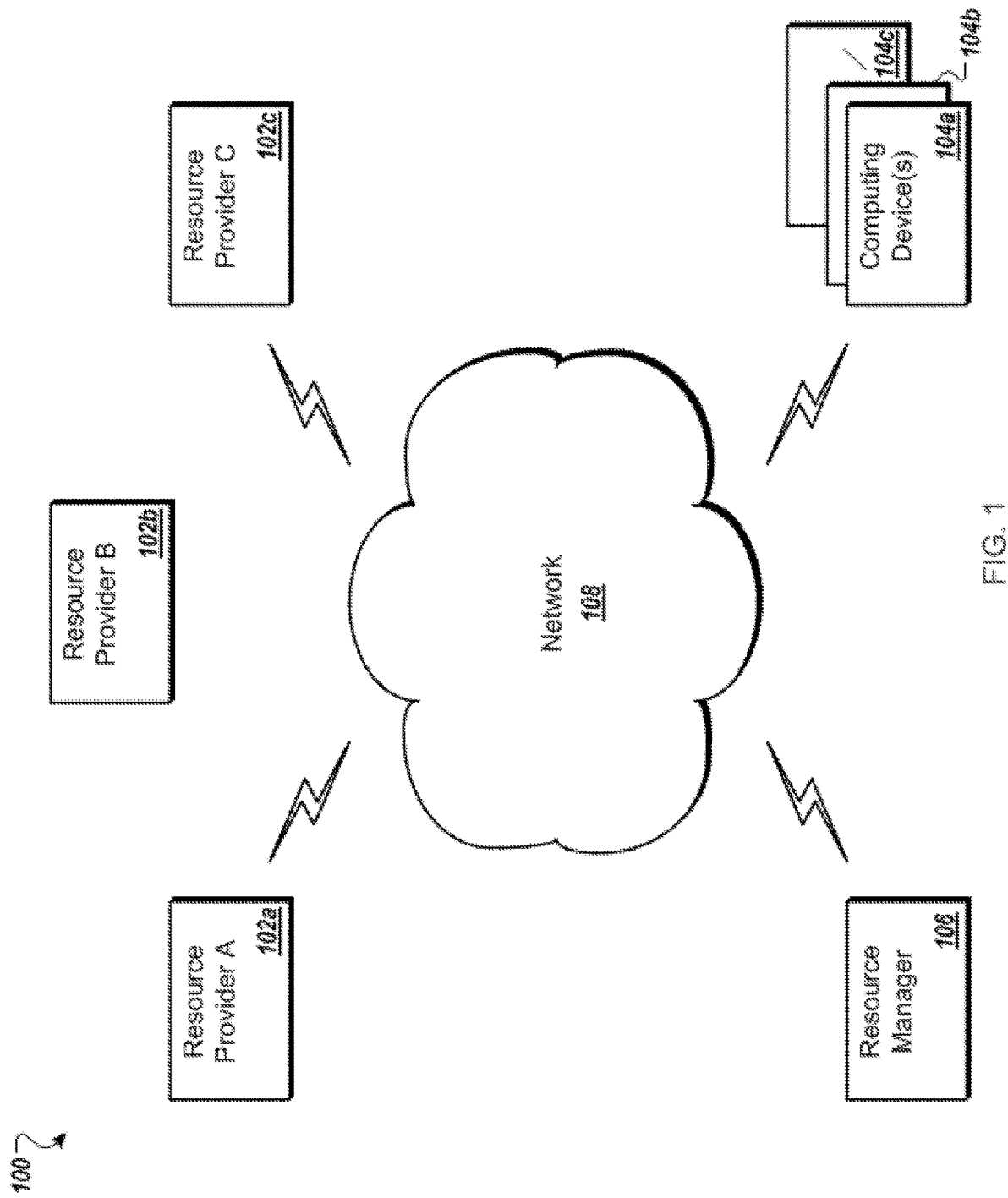
FIG. 1 is a block diagram of an example network environment for use in the methods and systems for customizing cell culture media for optimized cell proliferation based on genotyping data, according to an illustrative embodiment.

Throughout the description, where compositions are described as having, including, or comprising specific components, or where methods are described as having, including, or comprising specific steps, it is contemplated that, additionally, there are compositions of the present invention that consist essentially of, or consist of, the recited components, and that there are methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Presented herein are systems and methods for customizing cell culture media for optimized cell proliferation based on genetic traits of the cells. Factors of the cells, such as genetics, can determine the optimum cell culture conditions for growth and use of individual cells in vitro.

In certain embodiments, data corresponding to a plurality of genotyping data comprising measured SNPs and measured genes, derived from one or more biological samples supplied by a population of cells, can be associated with one or more genetic traits. Accordingly, a composition for a cell culture media based at least in part on the genotyping data can be selected for advantageous growth of the population of cells.

In certain embodiments, for each variant, genotyping data associated with the variant corresponds to an identification of a specific SNP variant. In certain embodiments, the genotyping data associated with the variant comprises an identification of a first nucleotide associated with a first copy (e.g., from a first of two sets of chromosomes) of a population of cell's genetic material, and an identification of a second nucleotide of a second copy (e.g., from a second of two sets of chromosomes) of a population of cell's genetic material (e.g., the measurement outcome comprises a two letter sequence, each letter identifying a particular nucleotide, e.g., the letter 'A' identifies adenine, the letter 'G' identifies guanine, e.g., the letter 'T' identifies thymine, e.g., the letter 'C' identifies cytosine).

SNPs correspond to specific locations within or nearby (e.g., a SNP may occur in a promotor region that influences transcription of a particular gene, e.g., a SNP may occur within 5 kb upstream or downstream of a particular gene, e.g., a SNP may occur within 100 kb upstream or downstream of a particular gene, e.g., a SNP may occur within 500 kb upstream or downstream of a particular gene, e.g., a SNP may occur within 1 Mb upstream or downstream of a particular gene) genes in a population of cell's genetic material.

In certain embodiments, for each biological sample (e.g., a population of cells), the genotyping data of the one or more SNPs comprise(s), for each SNP, a first measurement that identifies a first nucleotide of a first copy (e.g., from a first of two sets of chromosomes) of a population of cell's genetic material, and a second measurement that identifies a second nucleotide of a second copy (e.g., from a second of two sets of chromosomes) of a population of cell's genetic material. In certain embodiments, the genotyping data comprises data from a PCR-based SNP genotyping assay. Other genotyping assays can be performed to obtain the genotyping data. For example, other methods of genotyping include RFLPI (restriction fragment length polymorphism identification), RAPD (random amplified polymorphic detection), AFLPD (amplified fragment length polymorphism detection, DNA sequencing, and use of allele specific oligonucleotide (ASO) probes and/or hybridization to DNA microarrays.

In certain embodiments, the method comprises measuring, via a PCR-based SNP genotyping assay, one or more SNPs for a plurality of biological samples, thereby producing genotyping data.

Cell Culture Media Supplements
Albumins and Transport Proteins

In certain embodiments, the type, level, or concentration of albumin and/or transport proteins contained in cell culture media is adjusted based on the genetics of the cell line to be cultured. In certain embodiments, the albumin and/or transport proteins whose concentration can be adjusted include albumin human recombinant, bovine serum albumin (BSA), fetal bovine serum (FBS), conalbumin, fetuin from FBS, bovine transferrin, transferrin from human serum, apotransferrin bovine, holo-transferrin bovine, and holo-transferrin human.

Antibiotics

In certain embodiments, the type, level, or concentration of antibiotics contained in cell culture media is adjusted based on the genetics of the cell line to be cultured. In certain embodiments, the antibiotics whose concentration can be adjusted include Actinomycin D, Amphotericin B, Ampicillin, Carbenicillin, Chloramphenicol, Erythromycin, G 418, Gentamicin, Guanidine, Hygromycin B, Kanamycin, Mitomycin C, Mycophenolic acid, Neomycin, Nystatin, Penicillin G, Penicillin G, Polymyxin B, Puromycin, Spectinomycin, Streptomycin, and Streptomycin.

Cytokines and Growth Factors

In certain embodiments, the type, level, or concentration of cytokines and growth factors contained in cell culture media is adjusted based on the genetics of the cell line to be cultured. In certain embodiments, the cytokines and growth factors whose concentration can be adjusted include epidermal growth factors and NRG family members, fibroblast growth factors, growth factor analogs, hematopoietic cytokines, hepatocyte growth factor/scatter factors, humankine growth factors and cytokines, insulin-like growth factors, interleukins, macrophage inflammatory proteins, neurotrophic factors, platelet derived growth factors and hormones, transforming growth factors, tumor necrosis factor and family members, and vascular endothelial growth factor.

Hormones

In certain embodiments, the type, level, or concentration of hormones contained in cell culture media is adjusted based on the genetics of the cell line to be cultured. In certain embodiments, the hormones whose concentration can be adjusted include Dexamethasone, Erythropoietin, β-Estradiol, Hydrocortisone, Insulin, Progesterone, Prolactin (human), Somatostatin, L-Thyroxine, and 3,3',5-Triiodo-L-thyronine.

Lipids and Lipid Carriers

In certain embodiments, the type, level, or concentration of lipids and/or lipid carriers contained in cell culture media is adjusted based on the genetics of the cell line to be cultured. In certain embodiments, the lipids and/or lipid carriers whose concentration can be adjusted include cyclodextrins, Arachidonic acid, Cholesterol, Cod liver oil fatty acid methyl esters, Fatty Acid Supplements, Linoleic acid, Linoleic Acid-Oleic Acid-Albumin, and Oleic Acid.

Amino Acids

In certain embodiments, the type, level, or concentration of amino acids contained in cell culture media is adjusted based on the genetics of the cell line to be cultured. In certain embodiments, the amino acids whose concentration can be adjusted include N-Acetyl-L-cysteine, Ala-Gln, L-Alanine, L-Arginine, L-Asparagine, L-Cysteine, L-Glutamic acid, DL-Glutamic acid, L-Glutamine, L-Glutathione, Glycine, L-Histidine, trans-4-Hydroxy-L-proline, L-Isoleucine, L-Leucine, L-Lysine, L-Methionine, DL-Methionine, L-Phenylalanine, L-Proline, L-Serine, DL-Serine, L-Threonine, DL-Threonine, L-Tryptophan, L-Tyrosine, and L-Valine.

For example, L-Glutamine is an essential amino acid required by virtually all mammalian and insect cells grown in culture. Once deaminated, L-Glutamine is used as an energy source, incorporated into protein, and used in nucleic acid metabolism. L-Alanyl-L-Glutamine is a dipeptide derivative of L-glutamine, L-alanyl-L-glutamine incorporates L-alanine which protects the unstable alpha amino acid group. Aminopeptidases within the cells cleave the dipeptide, gradually releasing both L-glutamine and L-alanine for use by the cell.

Vitamins

In certain embodiments, the type, level, or concentration of vitamins contained in cell culture media is adjusted based on the genetics of the cell line to be cultured. The group of vitamins is a little noticed target for media optimization. Although the concentrations of these components are low, the availability of vitamins is quite important for the cells, since cells are known to have trouble producing vitamins on their own. Vitamins act as co-factors for many enzymes and are essential for their function. Accordingly, the absence of vitamins in culture may lead to decrease in cell growth, cell death, or loss of productivity.

In certain embodiments, the type, level, or concentration of vitamins contained in cell culture media is adjusted based on the genetics of the cell line to be cultured. In certain embodiments, vitamins whose concentration can be adjusted based on the genetics of the cell include L-ascorbic acid, biotin powder, Menadione sodium bisulfite, pyridoxamine dihydrochloride, retinyl acetate, RPMI 1640 Vitamins, (+)-Sodium L-ascorbate, and Beta Carotene, Vitamin A, Vitamin B12, Vitamin D, Folate levels, Vitamin B6, Vitamin E, and Vitamin C.

Vitamin B12

Vitamin B12 is the generic name for a family of cobalamin molecules responsible for growth, genetic stability and survival of cells in vitro. Members of this family are interchangeable and have different axial ligands and cobalt oxidation levels. As unique coenzymes of methionine synthase (EC 2.1.1.13) and methylmalonyl-CoA mutase (EC 5.4.99.2), the Vitamin B12 cobalamins, methylcobalamin and 5'-adenosylcobalamin, support one-carbon metabolism and the degradation of amino and odd-chain fatty acids, respectively. Vitamin B12 deficiency in vitro may contribute to acidosis, genome instability, and mitochondria-mediated apoptosis.

Vitamin B12 in cell culture media provides the following functions: one-carbon metabolism, S-Adenosyl Methionine, apoptosis, Proprionyl-CoA Metabolism, Cobalamin Delivery and Metabolism, and Cobalamin Transport.

Cultured cells require picomolar levels of physiological Vitamin B12. Vitamin B12 supplementation concentrations range from 0 to 7.4 µM in non-proprietary commercially available classic media. Most classic media were developed with sera, especially fetal bovine sera (FBS), as standard supplements. Sera contain Vitamin B12; however, the amounts of Vitamin B12 present in sera vary among species and with storage and handling. Further, variations of Vitamin B12 present in sera partially explain the wide range of Vitamin B12 found in classic media formulations. Chemical instability of Vitamin B12 in cell culture media also contributes to the wide range of supplementation levels.

The following classic media contain no Vitamin B12 in their basal formulations: Ames' Medium; Basal Medium Eagle (BME); Click's Medium; CMRL-1066 Medium: Dulbecco's Adjusted Eagle's Medium (DMEM); Fischer's Medium; Glasgow Adjusted Eagle's Medium (GMEM); L-15 Medium; Medium 199; Minimum Essential Medium, Eagle (EMEM); and Swim's S-77 Medium.

NCTC Medium contains very high levels of Vitamin B12, 7.4 µM.

RPMI-1640 and Iscove's Adjusted Dulbecco's Medium (IMDM) contain low levels of Vitamin B12, compared to other supplemented media, at 3.7 and 9.6 nM, respectively. Alpha-MEM contains 100 nM vitamin B12. IMDM and alpha-MEM are modifications of basal media that contain no vitamin B12. Waymouth Medium MB and Williams Medium E both contain 148 nM vitamin B12. H-Y Medium (Hybri-Max®) and McCoy's 5A Adjusted Medium contain 923 nM and 1.48 µM of vitamin B12, respectively. The high level of B12 present in H-Y Medium (Hybri-Max®) media derives from its NCTC component.

DMEM/Ham's Nutrient Mixture F-12 (50:50) is a basal media frequently used as a base for development of proprietary serum-free or protein-free cell culture media used for biomanufacturing of heterologous proteins, especially with Chinese Hamster Ovary (CHO) cells. It contains 501 nM of Vitamin B12 which derives from its F-12 component. Nutrient Mixture, Ham's F-10 and Nutrient Mixture, Ham's F-12 were developed for clonal growth of CHO cells without use of FBS. These media and their derivatives: F-12 Coon's Modification; Nutrient Mixture Ham's F-12, Kaighn's Modification (F12K) and Serum-Free/Protein Free Hybridoma Medium all contain 1 µM Vitamin B12.

The relatively high level of vitamin B12 in serum-free hybrikdoma media; Hybri-Max® and Serum-Free/Protein Free Hybridoma Medium suggests that serum-free systems for monoclonal antibody production require significant supplementation of media with vitamin B12. Cells in culture require physiological Vitamin B12 in the pM concentration range. The presence of vitamin B12 in basal media at nm and µM levels indicates that its delivery via cell culture media is complex. An issue for serum-free formulations may relate to the chemical instability of Vitamin B12.

Cell Types

In certain embodiments, cell types that can be used in the present disclosure include, primary cells (e.g., hair follicle dermal papilla cells, neural stem cells, astrocytes, skeletal muscle cells, cardiomyocytes, immune cells (T cells, B cells, NK cells), epithelial cells), blood cells (e.g., peripheral blood mononuclear cells), stem cells, and inducible pluripotent stem cells.

Genes Associated With Vitamin Deficiency

In certain embodiments, genes that influence genetic traits relating to cell proliferation in cell culture media include BCM01, FUT2, GC, MTHR, NBF2, RSU1, and SLC23A1.

Illustrative Network Environment

FIG. 1 shows an illustrative network environment 100 for use in the methods and systems for customizing cell culture media for optimized cell proliferation based on genotyping data of a sample, as described herein. In brief overview, referring now to FIG. 1, a block diagram of an exemplary cloud computing environment 100 is shown and described. The cloud computing environment 100 may include one or more resource providers 102a, 102b, 102c (collectively, 102). Each resource provider 102 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 102 may be connected to any other resource provider 102 in the cloud computing environment 100. In some implementations, the resource providers 102 may be connected over a computer network 108. Each resource provider 102 may be connected to one or more computing device 104a, 104b, 104c (collectively, 104), over the computer network 108.

The cloud computing environment 100 may include a resource manager 106. The resource manager 106 may be connected to the resource providers 102 and the computing devices 104 over the computer network 108. In some implementations, the resource manager 106 may facilitate the provision of computing resources by one or more resource providers 102 to one or more computing devices 104. The resource manager 106 may receive a request for a computing resource from a particular computing device 104. The resource manager 106 may identify one or more resource providers 102 capable of providing the computing resource requested by the computing device 104. The resource manager 106 may select a resource provider 102 to provide the computing resource. The resource manager 106 may facilitate a connection between the resource provider 102 and a particular computing device 104. In some implementations, the resource manager 106 may establish a connection between a particular resource provider 102 and a particular computing device 104. In some implementations, the resource manager 106 may redirect a particular computing device 104 to a particular resource provider 102 with the requested computing resource.

Figure 2:
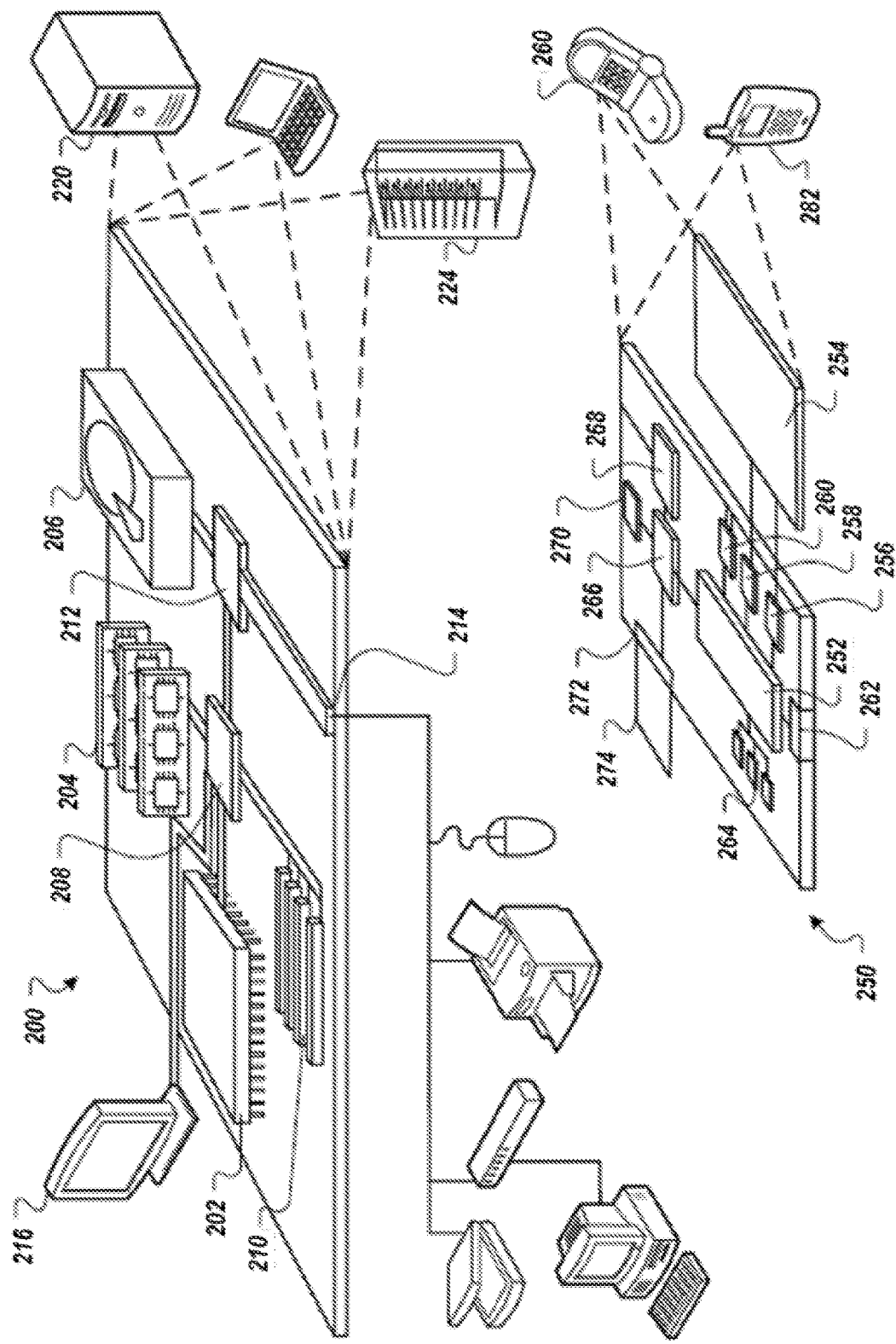
FIG. 2 is a block diagram of an example computing device and an example mobile computing device, for use in illustrative embodiments of the invention.

FIG. 2 shows an example of a computing device 200 and a mobile computing device 250 that can be used in the methods and systems described in this disclosure. The computing device 200 is intended to represent various forms of digital computers, such as laptops, desktops, workstations, personal digital assistants, servers, blade servers, mainframes, and other appropriate computers. The mobile computing device 250 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 200 includes a processor 202, a memory 204, a storage device 206, a high-speed interface 208 connecting to the memory 204 and multiple high-speed expansion ports 210, and a low-speed interface 212 connecting to a low-speed expansion port 214 and the storage device 206. Each of the processor 202, the memory 204, the storage device 206, the high-speed interface 208, the high-speed expansion ports 210, and the low-speed interface 212, are interconnected using various busses, and may be mounted on a common motherboard or in other manners as appropriate. The processor 202 can process instructions for execution within the computing device 200, including instructions stored in the memory 204 or on the storage device 206 to display graphical information for a GUI on an external input/output device, such as a display 216 coupled to the high-speed interface 208. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 204 stores information within the computing device 200. In some implementations, the memory 204 is a volatile memory unit or units. In some implementations, the memory 204 is a non-volatile memory unit or units. The memory 204 may also be another form of computer-readable medium, such as a magnetic or optical disk.

The storage device 206 is capable of providing mass storage for the computing device 200. In some implementations, the storage device 206 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 202), perform one or more methods, such as those described above. The instructions can also be stored by one or more storage devices such as computer- or machine-readable mediums (for example, the memory 204, the storage device 206, or memory on the processor 202).

The high-speed interface 208 manages bandwidth-intensive operations for the computing device 200, while the low-speed interface 212 manages lower bandwidth-intensive operations. Such allocation of functions is an example only. In some implementations, the high-speed interface 208 is coupled to the memory 204, the display 216 (e.g., through a graphics processor or accelerator), and to the high-speed expansion ports 210, which may accept various expansion cards (not shown). In the implementation, the low-speed interface 212 is coupled to the storage device 206 and the low-speed expansion port 214. The low-speed expansion port 214, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 200 may be implemented in a number of different forms, as shown in the figure. For example, it may be implemented as a standard server 220, or multiple times in a group of such servers. In addition, it may be implemented in a personal computer such as a laptop computer 222. It may also be implemented as part of a rack server system 224. Alternatively, components from the computing device 200 may be combined with other components in a mobile device (not shown), such as a mobile computing device 250. Each of such devices may contain one or more of the computing device 200 and the mobile computing device 250, and an entire system may be made up of multiple computing devices communicating with each other.

The mobile computing device 250 includes a processor 252, a memory 264, an input/output device such as a display 254, a communication interface 266, and a transceiver 268, among other components. The mobile computing device 250 may also be provided with a storage device, such as a micro-drive or other device, to provide additional storage. Each of the processor 252, the memory 264, the display 254, the communication interface 266, and the transceiver 268, are interconnected using various buses, and several of the components may be mounted on a common motherboard or in other manners as appropriate.

The processor 252 can execute instructions within the mobile computing device 250, including instructions stored in the memory 264. The processor 252 may be implemented as a chipset of chips that include separate and multiple analog and digital processors. The processor 252 may provide, for example, for coordination of the other components of the mobile computing device 250, such as control of user interfaces, applications run by the mobile computing device 250, and wireless communication by the mobile computing device 250.

The processor 252 may communicate with a user through a control interface 258 and a display interface 256 coupled to the display 254. The display 254 may be, for example, a TFT (Thin-Film-Transistor Liquid Crystal Display) display or an OLED (Organic Light Emitting Diode) display, or other appropriate display technology. The display interface 256 may comprise appropriate circuitry for driving the display 254 to present graphical and other information to a user. The control interface 258 may receive commands from a user and convert them for submission to the processor 252. In addition, an external interface 262 may provide communication with the processor 252, so as to enable near area communication of the mobile computing device 250 with other devices. The external interface 262 may provide, for example, for wired communication in some implementations, or for wireless communication in other implementations, and multiple interfaces may also be used.

The memory 264 stores information within the mobile computing device 250. The memory 264 can be implemented as one or more of a computer-readable medium or media, a volatile memory unit or units, or a non-volatile memory unit or units. An expansion memory 274 may also be provided and connected to the mobile computing device 250 through an expansion interface 272, which may include, for example, a SIMM (Single In Line Memory Module) card interface. The expansion memory 274 may provide extra storage space for the mobile computing device 250, or may also store applications or other information for the mobile computing device 250. Specifically, the expansion memory 274 may include instructions to carry out or supplement the processes described above, and may include secure information also. Thus, for example, the expansion memory 274 may be provided as a security module for the mobile computing device 250, and may be programmed with instructions that permit secure use of the mobile computing device 250. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 252), perform one or more methods, such as those described above. The instructions can also be stored by one or more storage devices, such as one or more computer- or machine-readable mediums (for example, the memory 264, the expansion memory 274, or memory on the processor 252). In some implementations, the instructions can be received in a propagated signal, for example, over the transceiver 268 or the external interface 262.

The mobile computing device 250 may communicate wirelessly through the communication interface 266, which may include digital signal processing circuitry where necessary. The communication interface 266 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 268 using a radio-frequency. In addition, short-range communication may occur, such as using a Bluetooth®, Wi-Fi™, or other such transceiver (not shown). In addition, a GPS (Global Positioning System) receiver module 270 may provide additional navigation- and location-related wireless data to the mobile computing device 250, which may be used as appropriate by applications running on the mobile computing device 250.

The mobile computing device 250 may also communicate audibly using an audio codec 260, which may receive spoken information from a user and convert it to usable digital information. The audio codec 260 may likewise generate audible sound for a user, such as through a speaker, e.g., in a handset of the mobile computing device 250. Such sound may include sound from voice telephone calls, may include recorded sound (e.g., voice messages, music files, etc.) and may also include sound generated by applications operating on the mobile computing device 250.

The mobile computing device 250 may be implemented in a number of different forms, as shown in the figure. For example, it may be implemented as a cellular telephone 280. It may also be implemented as part of a smart-phone 282, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Constructive Experimental Example

The present example describes how knowing the genetics and/or genetic traits of individual cell lines can help optimize cell growth and proliferation by providing cell culture media specific for the individual cell line. The present example describes how genotyping data can be used, for example, to identify Vitamin B12 deficiency in a particular cell line. Accordingly, a specific cell culture media that is known to be high in Vitamin B12 or a customized cell culture media with high Vitamin B12 concentration can be used to optimize growth and proliferation of cells. Other genetic traits of the cells can be identified and used to select and/or customize cell culture media for optimized growth and proliferation.

Based on genotyping data, various relevant cell culture media supplements that are of particular benefit to the population of cells can be identified. In certain embodiments, the identified cell culture media supplements can be provided (e.g., displayed, e.g., displayed via a graphic user interface) to a user who is culturing the population of cells.

In certain embodiments, where the genotyping data is based on SNP variants associated with identified traits, one or a combination of cell culture media products may be automatically recommended according to one or more identified traits (e.g., via reference to a look-up table or other mapping). In certain embodiments, the recommended cell culture media products are provided (e.g., displayed, e.g., displayed via a graphic user interface) to the user who is culturing the population of cells.

Figure 3:
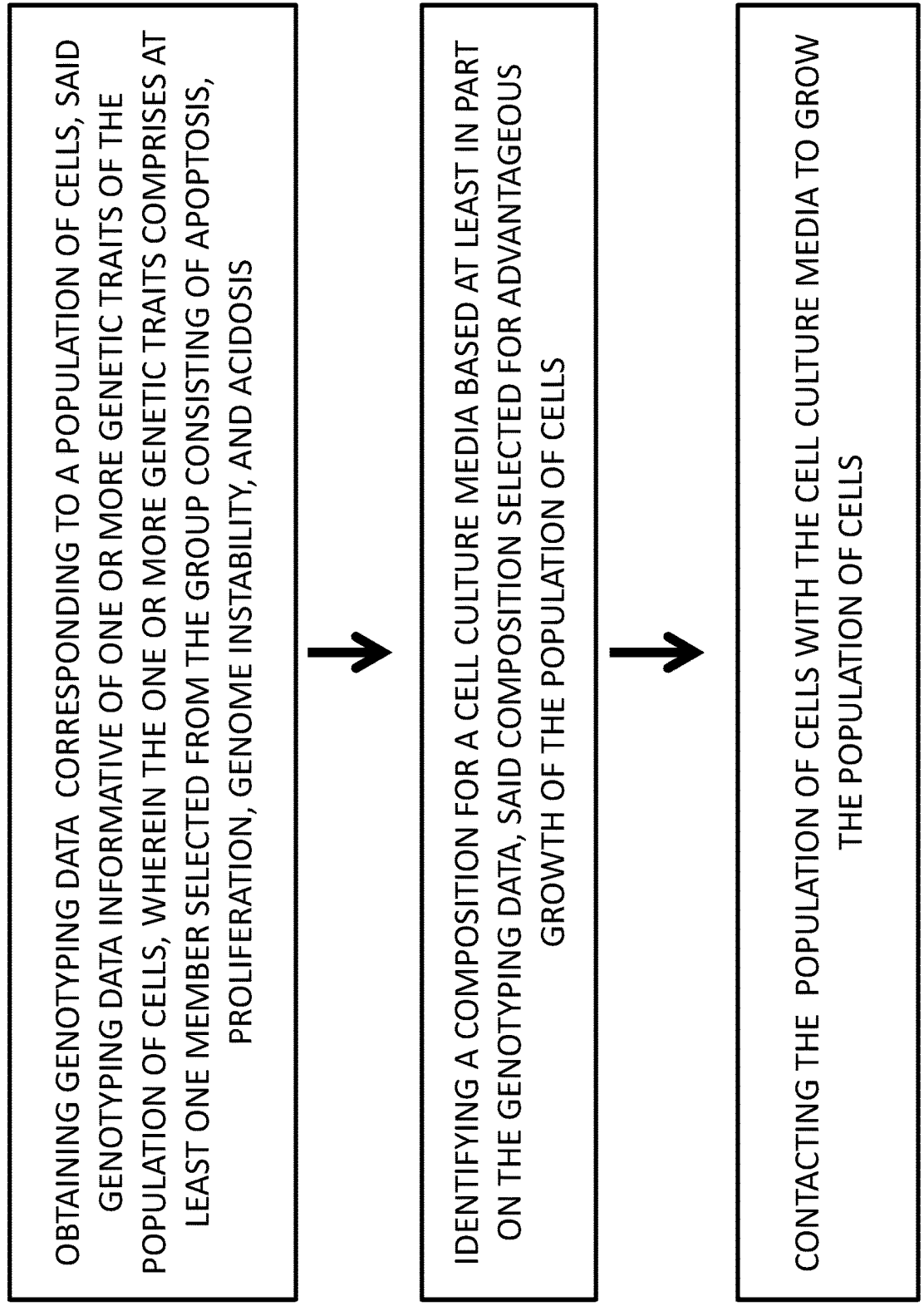
FIG. 3 shows a method for customizing cell culture media for optimized cell proliferation based on genetic traits of the cells, according to an illustrative embodiment of the invention.

FIGS. 3 and 4 each show a method for customizing cell culture media for optimized cell proliferation based on genetic traits of the cells, according to an illustrative embodiment of the invention.

Examples of such media that contain low levels or high levels of B12 are provided herein.

Examples of such media that contain low levels or high levels of different types of vitamins are provided herein.

What is claimed is:

1. A method comprising:
  accessing, by a processor of a computing device, genotyping data corresponding to a population of cells, said genotyping data informative of one or more genetic traits of the population of cells, wherein the one or more genetic traits comprise at least one member selected from the group consisting of apoptosis, proliferation, genome instability, and acidosis,
  wherein the genotyping data comprises measurements of one or more single-nucleotide polymorphisms (SNPs), wherein the one or more SNPs affect a cellular function encoded by a cellular maintenance gene or a cell cycle gene;
  automatically identifying, by the processor, a composition for a cell culture medium based at least in part on the genotyping data, said composition selected for advantageous growth of the population of cells; and
  contacting the population of cells with the cell culture medium to grow the population of cells.

2. The method of claim 1, wherein identifying a composition comprises:
  adjusting a level of one or more albumin and/or transport proteins in the cell culture medium based on the genotyping data of the population of cells.

3. The method of claim 2, wherein the one or more albumin and/or transport proteins comprise a member selected from the group consisting of albumin human recombinant, bovine serum albumin (BSA), fetal bovine serum (FBS), conalbumin, fetuin from FBS, bovine transferrin, transferrin from human serum, apo-transferrin bovine, holo-transferrin bovine, and holo-transferrin human.

4. The method of claim 1, wherein identifying a composition comprises:
  adjusting a level of one or more antibiotics in the cell culture medium based on the genotyping data of the population of cells.

5. The method of claim 4, wherein the one or more antibiotics comprise a member selected from the group consisting of actinomycin d, amphotericin b, ampicillin, carbenicillin, chloramphenicol, erythromycin, G418, gentamicin, guanidine, hygromycin b, kanamycin, mitomycin c, mycophenolic acid, neomycin, nystatin, penicillin g, polymyxin b, puromycin, spectinomycin, streptomycin, and streptomycin.

6. The method of claim 1, wherein identifying a composition comprises:
  adjusting a level of one or more cytokines and/or growth factors in the cell culture medium based on the genotyping data of the population of cells.

7. The method of claim 6, wherein the one or more cytokines and/or growth factors comprise a member selected from the group consisting of epidermal growth factors and neuregulin (NRG) family members, fibroblast growth factors, growth factor analogs, hematopoietic cytokines, hepatocyte growth factor/scatter factors, humankine growth factors and cytokines, insulin-like growth factors, interleukins, macrophage inflammatory proteins, neurotrophic factors, platelet-derived growth factors and hormones, transforming growth factors, tumor necrosis factor and family members, and vascular endothelial growth factor.

8. The method of claim 1, wherein identifying a composition comprises:
  adjusting a level of one or more hormones in the cell culture medium based on the genotyping data of the population of cells.

9. The method or claim 8, wherein the one or more hormones comprise a member selected from the group consisting of dexamethasone, erythropoietin, β-estradiol, hydrocortisone, insulin, progesterone, prolactin, somatostatin, L-thyroxine, and 3,3',5-triiodo-L-thyronine.

10. The method of claim 1, wherein identifying a composition comprises:
  adjusting a level of one or more lipids and/or lipid carriers in the cell culture medium based on the genotyping data of the population of cells.

11. The method of claim 10, wherein the one or more lipids and/or lipid carriers comprise a member selected from the group consisting of cyclodextrins, arachidonic acid, cholesterol, cod liver oil fatty acid methyl esters, fatty acid supplements, linoleic acid, linoleic acid-oleic acid-albumin, and oleic acid.

12. The method of claim 1, wherein identifying a composition comprises:
  adjusting a level of one or more amino acids in the cell culture medium based on the genotyping data of the population of cells.

13. The method of claim 12, wherein the one or more amino acids comprise a member selected from the group consisting of N-acetyl-L-cysteine, ala-gln, L-alanine, L-arginine, L-asparagine, L-cysteine, L-glutamic acid, DL-glutamic acid, L-glutamine, L-glutathione, glycine, L-histidine, trans-4-hydroxy-L-proline, L-isoleucine, L-leucine, L-lysine, L-methionine, DL-methionine, L-phenylalanine, L-proline, L-serine, DL-serine, L-threonine, DL-threonine, L-tryptophan, L-tyrosine, L-valine.

14. The method of claim 1, wherein identifying a composition comprises:
adjusting a level of one or more vitamins in the cell culture medium based on the genotyping data of the population of cells.

15. The method of claim 14, wherein the one or more vitamins comprise a member selected from the group consisting of L-ascorbic acid, biotin powder, menadione sodium bisulfite, pyridoxamine dihydrochloride, retinyl acetate, (+)-sodium L-ascorbate, beta-carotene, vitamin A, vitamin B12, vitamin D, folate, vitamin B6, vitamin E, and vitamin C.

16. The method of claim 1, comprising:
determining sensitivity of the population of cells to any of the following: transport proteins, antibiotics, growth factors, hormones, amino acids, and/or vitamins.

17. The method of claim 1, wherein the genotyping data for each SNP of the one or more SNPs comprises: a first measurement that identifies a first nucleotide at a location from a first of two sets of chromosomes of the population of cell's genetic material, and a second measurement that identifies a second nucleotide at the location from a second of two sets of chromosomes of the population of cell's genetic material.

18. The method of claim 1, wherein the one or more SNPs are associated with a gene selected from the group consisting of FADS1, KCTD10, BCMO1, FUT2, GC, NBF2, RSU1, and SLC23A1.

* * * * *